United States Patent [19]

Wissmann et al.

[11] 3,931,139

[45] Jan. 6, 1976

[54] TRIPEPTIDES HAVING AN ANTIDEPRESSIVE AND PROLACTIN-RELEASING ACTION

[75] Inventors: Hans Wissmann, Bad Soden, Taunus; Rolf Geiger, Frankfurt am Main; Wolfgang Konig, Langenhain, Taunus; Hansjorg Kruse, Kelkheim, Taunus; Karl Seeger, Hofheim, Taunus, all of Germany

[73] Assignee: Hoechst Aktiengesellschaft, Frankfurt am Main, Germany

[22] Filed: Aug. 22, 1974

[21] Appl. No.: 499,403

[30] Foreign Application Priority Data
Aug. 25, 1973  Germany............................ 2343035
Apr. 4, 1974   Germany............................ 2416428

[52] U.S. Cl....................... 260/112.5 TR; 424/177
[51] Int. Cl.²................. C07C 103/52; A61K 37/00
[58] Field of Search................................. 260/112.5

[56] References Cited
UNITED STATES PATENTS

| | | | |
|---|---|---|---|
| 3,725,380 | 4/1973 | Konig et al. | 260/112.5 |
| 3,795,666 | 5/1974 | Konig et al. | 260/112.5 |

OTHER PUBLICATIONS

Inouye et al.: Bull. Chem. Soc. Japan, 44, 1689–1691, (1971).
Rivier et al.: J. Med. Chem., 15, 479–482, (1972).
Chang et al.: J. Med. Chem., 14, 481–483, (1971).
Bowers et al.: Biochem. Biophys. Res. Comm., 40, 683–691, (1970).
Chang et al.: J. Med. Chem., 14, 484–487, (1971).

*Primary Examiner*—Lewis Gotts
*Assistant Examiner*—Reginald J. Suyat
*Attorney, Agent, or Firm*—Curtis, Morris & Safford

[57] ABSTRACT

The invention relates to tripeptide amides containing pyroglutamine, proline and histidine as amino acids having anti-depressive activity and a process for their manufacture.

7 Claims, No Drawings

TRIPEPTIDES HAVING AN ANTIDEPRESSIVE AND PROLACTIN-RELEASING ACTION

It is already known that the tripeptide

⌐Glu-his-pro-NH₂ (TRH) does not only aid the liberation of thyreotropic hormone but also the release of prolactin (German Offenlegungsschrift No. 2,253,274) and furthermore has an anti-depressive action (U.S. Pat. No. 3,737,549). However, the TRH which has been hitherto examined, especially with regard to the three actions mentioned, has the disadvantage of the strong thyreotropin -releasing effect when used as an anti-depressive drug and as a lactation-promoting factor.

It has now been found, surprisingly, that by a relatively small substitution in the TRH molecule, compounds may be prepared in which the TRH effect is insignificant, but the prolactin-releasing and anti-depressive action remains nearly unchanged. With these compounds there is no risk of hyperthyreosis.

The present invention relates to tripeptides of the general formula I

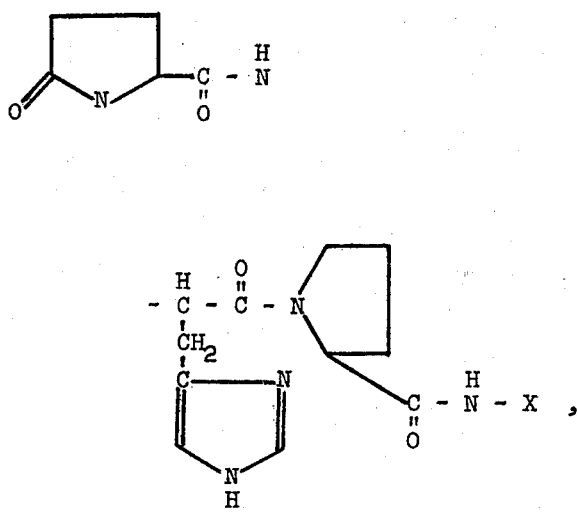

wherein X is alkyl having 2 to 8 carbon atoms, a cycloalkyl radical having 5 to 7 carbon atoms or an aralkyl radical having 1 or 2 carbon atoms in the alkyl portion.

The invention further relates to a process for preparing these peptides, wherein either a. Z-Histidine-azide is reacted with a proline derivative of the general formula II

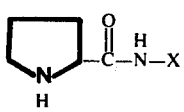

(II)

wherein X has the above meaning and Z is the benzylcarboxy radical, the N radical Z is subsequently removed by hydrogenation and the compound formed is reacted with a pyroglutamic acid active ester or b. Z-Gln(MbH)-his-OH is reacted with a proline derivative of the general formula II with addition of DCC and 1-hydroxybenzotriazol and the protected tripeptides obtained are treated with trifluoro-acetic acid/anisol.

Method (a) describes the stepwise build-up. According to this method, the Z-his-hydrazide is converted into the Z-his-azide and reacted with the proline amides of the general formula II to give Z-his-pro-NH-X. By catalytic hydrogenation in methanol, the radical Z is split off. With the addition of 1N methanolic hydrochloric acid a pH-value of 4 is maintained with the aid of an autotitrator. Then the reaction product can be reacted with a pyroglutamic acid active ester to form the compounds of the invention. For example the 4-nitro-phenyl-, pentachloro-phenyl or the 2,4,5-trichloro-phenyl ester may be used.

In this step there may be used as solvents preferably strongly polar solvents such as dimethylformamide, dimethylacetamide or dimethylsulfoxide. To increase the reaction speed there may also be added in the last condensation step acidic N-hydroxy compounds, as for example 1-hydroxybenzotriazole, 3-hydroxy-4-oxo-3,4-dihydro-quinazoline or 1-hydroxy-pyridone-2.

According to method (b) the Z-Gln (MbH)-his-OH is reacted with the proline compounds of the general formula II with the aid of DCC and 1-hydroxy-benzotriazole. The resulting tripeptides may be converted into the compounds of the invention by boiling (about 90 minutes) in a mixture of trifluoroacetic acid/anisol (9:1). The free base may be obtained from the trifluoroacetate by means of an alkaline ion exchanger.

The compounds of the invention are drugs which increase the prolactin level in the blood and are used for the therapy of neurotic and psychotic diseases, especially of depressions.

They may be administered orally in the form of tablets or capsules or by intravenous or intramuscular injection in a dissolved state in a physiological sodium chloride solution. To increase the amount of milk these substances may be used above all for brood animals such as swine or cattle.

As dosage units there are considered for both indications perorally, 10 mg –0.25 mg/kg; by subcutaneous and intramuscular injection, 0.015 mg – 0.0004 mg/kg; by intravenous injection, 0.01 mg – 0.00025 mg/kg. The parenteral application is preferred with 0.001 mg/kg.

Abbreviations:

| | | | |
|---|---|---|---|
| ⌐Glu | Pyroglutamic acid | Tcp | Trichlorophenyl |
| Z | Benzyloxycarbonyl | HOBT | 1-hydroxy-benzotriazole |
| Mbh | 4,4'-dimethoxybenzhydryl | | |
| DCC | dicyclohexylcarbodiimide | | |

The following Examples illustrate the invention.

EXAMPLE 1

⌐Glu-his-pro-ethyl amide a. Z-Gln(Mbh)-his-pro-ethyl amide 2.6 ml of N-ethyl-morpholine and an ice-cold solution of 4.4 g of DCC dissolved in dimethylformamide were added at 0°C to a solution of 13 g (20 mmols) of Z-Gln(Mbh)-his-OH, 2.7 g (20 mmols) of HOBt and 3.6 g (20 mmols) of HCl.H-pro-ethyl amide in 50 ml of dimethylformamide. The mixture was stirred for 1 hour at 0°C and stirred over night at room temperature. The deposit was suction-filtered and the filtrate was evaporated. The residue was distributed between ethyl acetate and sodium bicarbonate solution. The ethyl acetate phase was washed again with water, dried over sodium sulfate and evaporated. The residue was triturated with ether and suction-filtered. The product obtained was reprecipitated from tetrahydrofurane/ether.

Yield: 13.6 g of an amorphous substance without sharp melting point.

b. ⌐Glu-his-pro-ethyl amide - $CH_3COOH \cdot H_2O$ 6.5 g of Z-Gln(Mbh)-his-pro-ethyl amide were refluxed in 50 ml of trifluoro-acetic acid/anisol (10:1) at a bath temperature of 80°C for 90 minutes and then evaporated. The residue was digested several times with ether and suction-filtered. The substance was dissolved in water, chromatographed over a strongly alkaline ion exchanger ("Serdolit Blau") and the eluate was freeze-dried.

Yield: 3.07 g.

For purification, 2 g of the substance were chromatographed over Sephadex LH 20. To prepare the column, first 400 ml of glacial acetic acid, 4 l of water and 800 ml of n-butanol were shaken 300 ml of the upper phase were stirred with 240 g of Sephadex LH 20, whereby the whole amount of the solvent was absorbed. The thus pre-treated column filling was suspended in a corresponding amount of the lower phase. The mixture was allowed to swell for 3 hours and the column was filled up. The product was eluted with the lower phase.

Yield of chromatographically pure product: 1.17 g, $[\alpha]_D^{20} = -45.1°$ ($c = 1$, in methanol).

EXAMPLE 2 a. Z-Pro-n-propyl amide 22 g of DCCI, dissolved in 50 ml of cold tetrahydrofuran were added at 0°C to a solution of 25 g of Z-Pro-OH (0.1 mol) and 13.5 g (0.1 mol) of HOBt and 5.9 g of n-propylamine in 250 ml of absolute tetrahydrofuran. The mixture was stirred for 1 hour at 0° and for 3 hours at room temperature. The deposit was suction-filtered and the filtrate was evaporated. The oily residue was dissolved in ethyl acetate and then extracted successively with a sodium bicarbonate solution, 2N hydrochloric acid, a sodium bicarbonate solution, and water, dried over sodium sulfate and evaporated. The residue was triturated with petroleum ether and suction-filtered. For purification it was dissolved in ethyl acetate and chromatographed over about 60 g of alkaline $Al_2O_3$. It was eluted with ethyl acetate. The eluate was evaporated and triturated with petroleum ether.

Yield: 18.8 g (65%). Melting point: 77° – 77.5°.

b. HCl-H-pro-n-propyl amide 18.5 of Z-Pro-n-propyl amide were dissolved in methanol and hydrogenated catalytically after addition of a Pd - catalyst. By addition of methanolic hydrochloric acid by means of an auto-titrator, a pH-value of 4.5 was maintained. When hydrogenation was finished the catalyst was suction-filtered and the filtrate was evaporated. 12.4 g of an oil remained.

c. Z-Gln(Mbh)-his-pro-n-propyl amide 4.2 ml of N-ethyl-morpholine and an ice-cold solution of 4.4 g of DCC dissolved in a small amount of dimethylformamide were added at 0°C to a solution of 21.5 g (32.3 mols) of Z-Gln(Mbh)-his-OH, 4.47 g (32.3 mmols) of HOBt and 6.2 g of HCl.H-pro-n-propyl amide in 50 ml of dimethylformamide. Stirring was continued as in Example 1 a.

Yield: 21.4 g of an amorphous substance without sharp melting point.

d. ⌐Glu-his-pro-$H_2O$ 6.5 g of Z-Gln(Mbh)-his-pro-n-propyl amide were reacted in analogous manner as described in Example 1 b. Yield: 3 g. 1.5 g were purified on Sephadex LH 20 in analogous manner as described in 1 b.

Yield of acetate: 1032.6 mg. Since the acetate was hygroscopic, it was dissolved in water and chromatographed over the ion exchanger "Serdolit Blau".

Yield: 770 mg $[\alpha]_D^{20} = -52.5°$ ($c = 0.5$, in methanol).

EXAMPLE 3

⌐Glu-his-pro-isobutyl amide a. Z-Pro-isobutyl amide

The procedure was carried out as described in Example 2a: instead of n-propyl-amide 7.3 g of isobutyl amide were used.

Yield: 23.8 g, melting point 89° – 90°C.

b. HCl.H-Pro-isobutyl amide 23.5 g of Z-Pro-isobutyl amide were hydrogenated catalytically as described in Example 2 b.

Yield: 16.9 g of oil.

c. Z-Bln(Mbh)-his-pro-isobutyl-amide 5.3 ml of N-ethyl-morpholine and an ice-cold solution of 9 g of DCCI dissolved in dimethylformamide were added at 0°C to a solution of 27.3 g of Z-Gln(Mbh)-his-OH, 5.7 g of HOBt and 8.45 g of HCl.H-pro-isobutyl amide in 50 ml of dimethyl-formamide. Working up was carried out as described in Example 1a. Yield: 26.8 g of amorphous substance without sharp melting point.

d. ⌐Glu-his-pro-isobutyl amide . $H_2O$ 6.5 g of Z-Gln(Mbh)-his-pro-NH-isobutyl amide were reacted in analogous manner as in Example 1b.

Yield: 2.9 g.

1 g was purified in analogous manner as in Example 1 b on Sephadex LH 20 and subsequently chromatographed over ion exchanger "Serdolit Blau". Yield: 400 g of chromatographically pure substance. $[\alpha]_D^{20} = -58.2°$ ($c = 0.5$, in methanol).

EXAMPLE 4

⌐Glu-his-pro-n-pentyl amide a. Z-Pro-n-pentyl amide

The same procedure as in Example 2a was used: instead of n-propyl amine 8.8 g of n-pentyl amine, were used.

Yield: 27.3 g, melting point 70° – 72°C.

b. HCl.H-pro-n-pentyl amide 27 g of Z-Pro-n-pentyl amide were hydrogenated catalytically as described in Example 2 g. Yield: 16.7 g of oil.

c. Z-Gln(Mbh)-his-pro-n-pentyl amide 4.8 ml of N-ethyl-morpholine and an ice-cold solution of 8.3 g of DCC dissolved in dimethylformamide were added at 0°C to a solution of 24.4 g of Z-Gln(Mbh)-his-OH, 5.08 g of HOBt and 8.3 g of HCl.H-Pro-n-pentyl amide in 50 ml of dimethylformamide. Working up was carried out as described in Example 1a.

Yield: 22 g of amorphous substance without sharp melting point.

d. ⌐Glu-his-pro-n-pentyl amide . $H_2O$ 6.5 g of Z-Gln(Mbh)-his-pro-n-pentyl amide were reacted in analogous way as in Example 1b. Yield: 3.1 g. 3 g were purified in analogy to Example 1b on Sephadex LH 20 and then chromatographed over ion exchanger "Serdolit Blau".

Yield: 2.1 g.; $[\alpha]_D^{20} = -54.2°$ ($c = 1$, in methanol).

EXAMPLE 5 a. Z-Pro-β-phenylethyl amide 124.5 g (0.5 mol) of Z-Pro-OH were dissolved in 800 ml of tetrahydrofuran. After addition of 69.5 ml of triethyl amine the mixture was cooled, while stirring, to −10°C. Then 48 ml (0.5 mol) of chloroformic acid ethyl ester were added dropwise. Stirring was continued for 3 minutes at the temperature indicated, then the previously cooled solution of 60.5 g (0.5 mol) of β-phenylethyl amine in 200 ml of tetrahydrofuran were added, and stirring was continued for 20 minutes at 0°C and for 1.5 hours at room temperature. The crude product isolated at room temperature by evaporating the reaction solution under reduced pressure was purified with charcoal by taking up in ethyl acetate, extracting with saturated N—HCl, saturated $NaHCO_3$-solution and water and saturated N—HCl, saturated $NaHCO_3$-solution and water and subsequently clarifying the ethyl acetate solution, dried over $MgSO_4$ and crystallized by evaporation under reduced pressure. After recrystallization from methylene chloride/petroleum ether, 137 g (78%) having a solidification point of 89° – 91°C were obtained.

$[\alpha]_D^{20} = -53°$ ($c = 1$, ethanol).

b. H-Pro-β-phenylethyl amide . HCl 135 g (0.382 mol) of Z-Pro-β-phenylethyl amide were dissolved in 1 liter of methanol and hydrogenated as usual with addition of a 1N-methanolic hydrochloric acid at pH 3.5 with a 10 % $Pd/BaSO_4$ - catalyst. After 3 hours the hydrogenation was completed. The mixture was evaporated under reduced pressure at room temperature. The remaining solid substance was dried under reduced pressure and then triturated with ether.

Yield: 95 g; solidification point 143° – 146°C $[\alpha]_D = -53.3°C$ ($c = 1$, ethanol).

c. Z-his-pro-β-phenylethyl amide 38.2 g (0.15 mol) of H-pro-β-phenylethyl amide. HCl were dissolved in 300 ml of chloroform and extracted several times with a $2N-Na_2CO_3$-solution and then with water. The chloroform solution was evaporated under reduced pressure after drying over $MgSO_4$. The resulting oil was taken up in ethyl acetate and cooled to −5°C. A solution of 45.5 g of Z-his-hydrazide in 600 ml of N-HCl was cooled to 0°C. 34.5 ml of aqueous 5N sodium nitrite solution at 0°C were added dropwise. Stirring was continued for 4 minutes at 0°C, then 300 ml of precooled ethyl acetate were added. The aqueous phase of the reaction mixture was adjusted to pH 9 with cooled 2N sodium carbonate solution; after transferring the reaction mixture to a cooled separatory funnel, the ethyl acetate phase was separated and dried for a short time over magnesium sulfate together with two further ethyl acetate extracts of the reaction mixture. After filtration from the drying agent, it was added at 0°C to the above-described solution of H-pro-β-phenylethyl amide.

The reaction mixture was stirred for 2 hours at 0°C and allowed to stand over night at +4°C. After filtration from a small amount of difficultly soluble material, the mixture was washed with a sodium bicarbonate solution and water, dried over $MgSO_4$, and evaporated under reduced pressure at room temperature. The solid residue was dissolved in 100 ml of methylene chloride and converted into the hydrochloride by addition of a solution of anhydrous hydrochloric acid. Yield after precipitation with absolute ether: 35.9 g.

Solidification point: 108°C (Z), $[\alpha]_D = -51.2°$ ($c = 1$, ethanol).

d. H-his-pro-β-phenylethyl amide, 2 HCl 35 g of Z-his-pro-β-phenylethyl amide were dissolved in 400 ml of methanol, mixed with 10 % of a $Pd/BaSO_4$ catalyst and hydrogenated as usual with a 1N-methanolic hydrochloric acid, while maintaining a constant pH-value of 3.5. After evaporating the filtered solution under reduced pressure at room temperature and triturating the residue with absolute ether, the dipeptide-amide-hydrochloride was obtained with a practically quantitative yield.

Solidification point: 161° (Z) $[\alpha]_D = -64.2°$ ($c = 1$, $CH_3OH$).

e. ⌐Glu-his-pro-β-phenylethyl amide 10.18 g (0.033 mol) of pyroglutamic acid-2,4,5-trichlorophenyl ester in 30 ml of DMF were added at 0°C to a solution of 12.84 g (0.03 mol) of H-His-pro-β-phenylethyl amide . 2 HCl and 7.6 ml (0.06 mol) of N-ethylmorpholine in 90 ml of DNF. Stirring was continued for 3 hours at this temperature and the mixture was allowed to stand for 20 hours at +4°C. Then it was evaporated at room temperature under reduced pressure, and the residue was digested with absolute ether. The crude product thus obtained was recrystallized from ethanol.

Yield: 9.4 g, solidification point 121°C . $[\alpha]_D = -24.6°C$ ($c = 0.5$, DMF/ethanol 1:1).

EXAMPLE 6 a. Z-Pro-n-hexyl amide 50 g (0.1 mol) of Z-Pro-OH were dissolved in 400 ml of anhydrous tetrahydrofuran, 28 ml of triethyl amide were added. The mixture was cooled to −10° and then 19.5 ml (0.2 mol) of chloroformic acid ethyl ester were added dropwise. After stirring for 10 minutes at −10°C, 96 ml (1 mol) of n-hexyl amine were added portionwise at this temperature, and the whole was stirred for another 6 hours without cooling. Subsequently it was evaporated under reduced pressure and taken up with ethyl acetate. The ethyl acetate solution was extracted with a 5 % $KHSO_4$-solution, saturated $NaHCO_3$-solution and water. After evaporating the ethyl acetate solution, dried over sodium sulfate, the product was crystallized.

Yield: 55.5 g (83.5 %) Solidification point: 60°C.

b. H-Pro-n-hexylamide . HCl 50 g of Z-Pro-n-hexyl amide were hydrogenated as usual in a methanolic solution in the presence of 10 % of a $Pd/BaSO_4$ catalyst and with titration of the released amino groups with methanol . HCl ($P_H$ 4.0). Yield after filtration from the catalyst and evaporation of the methanol under reduced pressure at room temperature and subsequent digestion of the residue with absolute ether: 29 g of a colorless, viscous oil.

c. Z-his-pro-n-hexyl amide 15.1 g (0.05 mol) of Z-his-hydrazide were dissolved in 200 ml of N-HCl and, at 0°C, 11.5 ml of a 5N sodium nitrite solution were added dropwise. After stirring for 4 minutes at 0°C, the solution was covered by a layer of ethyl acetate at 0°C and alkalized at 0°C with a cooled saturated sodium carbonate solution. After thoroughly mixing, the ethyl ester solution was separated. It was extracted twice and the combined ethyl acetate extracts were dried for a short time, while cooling, over anhydrous magnesium sulfate. The cooled dried ethyl acetate solution was added, while stirring, to a solution also cooled to 0°C of 11.6 g (0.05 mol) of H-pro-n-hexyl-amide . HCl and 6.6 ml of N-ethyl morpholine in 80 ml of DMF/methanol (8:2). After stirring for 2 hours at 0°C and allowing to stand for 16 hours at +4°C, the solvents were removed by distilling off under reduced pressure at room temperature. The residue was taken up in ethyl acetate, and the ethyl acetate solution was extracted several times with a saturated sodium carbonate solution and water. From the ethyl acetate solution thus purified and dried over MgSO₄ the final product was obtained after evaporating the solvent as a colorless oil.

Yield: 19 g = 81 % of the theory.

d. H-his-pro-n-hexyl amide . 2HCl 19 g of Z-his-pro-n-hexyl amide were dissolved in 200 ml of absolute methanol and hydrogenated as usual while using 10 % of a Pd/BaSO₄-catalyst. The released amino groups were filtered with 1N-methanol . HCl at $P_H$ 4.0. After 2.5 hours the hydrogenation was finished. The reaction product was precipitated with absolute ether after filtration from the catalyst and evaporation of the solution under reduced pressure at room temperature.

Yield: 15.4 g (94 %), Melting point: 164°C. $[\alpha]_D = -52.5°$ ($c = 1$, CH₃OH).

e. L-Glu-his-pro-n-hexyl amide

A solution of 3.7 g of Glu-OTcp in 15 ml of dimethylformamide was added at 0°C while stirring to a solution of amide. 4.06 g (0.01 mol) of H-his-pro-n-hexyl amide2 HCl and 2.52 ml (0.02 mol) of N-ethyl-morpholine in 40 ml of DMF. Stirring was continued for 1 hour at 0°C. The mixture was allowed to stand over night at +4°C and the reaction mixture was stirred for 5 hours at 0°C and for 2 hours at room temperature. The residue was digested with 60 ml of a mixture of ethyl acetate and saturated sodium carbonate solution. The insoluble salt was separated and taken up in ethanol. From the ethanol solution the final product was precipitated with absolute ether as a colorless hydroscopic solid substance.

Yield: 2.0 g Melting point: decomposition begins at 221°C. $[\alpha]_D = -41.3°$ ($c = 1$, CH₃OH).

The amino acid analysis after a 72 hours' hydrolysis with 6N-hydrochloric acid in a sealed tube at 110°C showed the following proportions of amino acid: Glu: 1.09, His: 0.92, Pro: 1.0.

EXAMPLE 7 a. Z-Pro-cyclohexyl amide

The preparation was carried out as described in Example 6a, but instead of n-hexyl-amine a cyclohexyl amine was used. The final product was recrystallized from methanol/water.

Yield: 33.4 g (50 % of the theory). Melting point: 146°C.

b. H-Pro-cyclohexyl amide-hydrochloride

The compound was prepared by hydrogenation of 33.4 g of Z-procyclohexyl amide as described under 6 b.

Yield: 19.8 g (practically quantitative). Melting Point: 213°C, $[\alpha]_D = -19.0°C$ ($c = 1$, DMF).

c. Z-His-Pro-cyclohexyl amide

The preparation was carried out as described in Example 6c, but instead of H-pro-n-hexyl amide the H-pro-cyclohexyl amide was used.

Yield: 18.6 g (80 % of the theory). Melting point: 103°C $[\alpha]_D = -48.2°$ ($c = 1$, CH₃OH).

d. Hi-his-pro-cyclohexyl-amide-dihydrochloride

A solution of 18.6 g of Z-his-pro-cyclohexyl amide in 200 ml of methanol was hydrogenated and worked up as described in Example 6 d.

Yield: 15.5 g (95 % of the theory). Melting point: 152° (decomposition $[\alpha]_D = -53.8°C$ ($c = 1$, CH₃OH).

e. L-Glu-his-pro-cyclohexyl amide

The preparation was carried out as described in Example 6e; instead of H-his-pro-n-hexyl amide the H-his-pro-cyclohexyl amide was used.

Yield: 2.0 g Melting point: decomposition begins at 192°C $[\alpha]_D = -4.6°C$ ($c = 1$, CH₃OH)

Amino acid analysis (after a 72 hours' hydrolisis with 6N-HCl in the sealed tube at 110°C):

L-Glu: 1.08; His: 0.97; Pro: 1.0.

EXAMPLE 8

(method b)

a. Z-Gln(Mbh)-his-pro-n-hexyl amide 1.3 ml of N-ethyl-morpholine and at 0°C 2.2 g of DCC were added to a solution of 6.5 g of Z-Gln(Mbh)-his-OH, 1.35 g of 1-hydroxy-benzotriazole and 2.35 g of proline-n-hexyl amide-hydrochloride in 50 ml of DMF. The mixture was stirred for 1 hour at 0°C and over night at room temperature. The deposit was suction-filtered and the filtrate was evaporated. The residue was distributed between ethyl acetate, to which a small amount of dimethylformamide was added, and a sodium carbonate solution. The ethyl acetate solution was dried with sodium sulfate and evaporated. The residue was triturated with ether.

Yield: 7.1 g of amorphous substance.

b. L-Glu-his-pro-n-hexyl amide 4.1 g of Z-Gln(Mbh)-his-pro-n-hexyl amide were dissolved in 20 ml of trifluoroacetic acid/anisol (9:1) and refluxed for 90 minutes. The trifluoroacetic acid was evaporated and the residue was distributed between water and ether. The aqueous solution was clarified with a small amount of charcoal and filtered over an alkaline ion exchanger. The alkaline eluate was freeze-dried.

Yield: 1.8 g.

The product was identical with the substance obtained according to Example 6e.

What we claim is:

1. A tripeptide of the formula

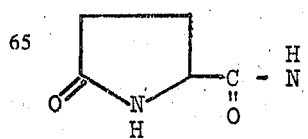

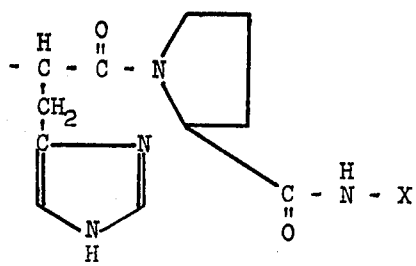

wherein X is alkyl having 3 to 8 carbon atoms, cycloalkyl having 5 to 7 carbon atoms, or aralkyl having 1 or 2 carbon atoms in the alkyl portion thereof.

2. A tripeptide as in claim 1 wherein X is n-propyl.
3. A tripeptide as in claim 1 wherein X is isobutyl.
4. A tripeptide as in claim 1 wherein X is n-pentyl.
5. A tripeptide as in claim 1 wherein X is β-phenylethyl.
6. A tripeptide as in claim 1 wherein X is n-hexyl.
7. A tripeptide as in claim 1 wherein X is cyclohexyl.

* * * * *